United States Patent
Lounis et al.

(10) Patent No.: US 7,889,343 B2
(45) Date of Patent: Feb. 15, 2011

(54) METHOD AND SYSTEM FOR OPTICAL DETECTION OF NANO-OBJECTS IN A LIGHT REFRACTING MEDIUM

(75) Inventors: Brahim Lounis, Bordeaux (FR); Laurent Cognet, Bordeaux (FR); Stephane Berciaud, Pessac (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 512 days.

(21) Appl. No.: 11/631,621

(22) PCT Filed: Jul. 1, 2005

(86) PCT No.: PCT/FR2005/001704
§ 371 (c)(1),
(2), (4) Date: Sep. 6, 2007

(87) PCT Pub. No.: WO2006/013272
PCT Pub. Date: Feb. 9, 2006

(65) Prior Publication Data
US 2007/0296972 A1     Dec. 27, 2007

(30) Foreign Application Priority Data
Jul. 7, 2004   (FR) .................................. 04 07548

(51) Int. Cl.
*G01J 4/00*   (2006.01)
*G01N 21/41*  (2006.01)
*G30G 5/16*   (2006.01)

(52) U.S. Cl. ...................... 356/432; 356/364; 356/445; 250/316.1; 250/339.14; 250/341.1

(58) Field of Classification Search ......... 356/432–444, 356/450, 503, 364–369, 129; 250/431.6, 250/316.1, 339.14, 341.1, 358.1; 374/43, 374/124, 126, 130; 435/4, 6, 7.1
See application file for complete search history.

(56) References Cited

U.S. PATENT DOCUMENTS

| | | | | |
|---|---|---|---|---|
| 4,076,420 A | * | 2/1978 | De Maeyer et al. | 356/73 |
| 5,434,878 A | * | 7/1995 | Lawandy | 372/43.01 |
| 6,506,342 B1 | * | 1/2003 | Frankel | 506/31 |
| 6,756,591 B1 | * | 6/2004 | Lounis et al. | 250/316.1 |
| 6,871,527 B2 | * | 3/2005 | Hansma et al. | 73/105 |
| 6,965,434 B2 | * | 11/2005 | Lounis et al. | 356/450 |
| 6,975,898 B2 | * | 12/2005 | Seibel | 600/473 |

* cited by examiner

*Primary Examiner*—Sang Nguyen
(74) *Attorney, Agent, or Firm*—Young & Thompson

(57) ABSTRACT

Method and system for optical detection of nano-objects in a refracting medium. A nano-object ($n\_o_i$) and the refractive medium are illuminated (A) with a periodically amplitude modulated coherent electromagnetic heating wave ($HB(\Omega)$), to generate a specified temperature and refractive index profile in the vicinity of the nano-object, and with a coherent electromagnetic probe wave (PB) to generate an emerging probe wave ($EPB(\Omega)$) having at least one intensity component amplitude modulated by a beat at the modulation frequency of the coherent heating wave. The intensity component amplitude modulated by a beat is detected (C) in the emerging wave ($EPB(\Omega)$), to distinguish and represent this nano-object in the refractive medium. The invention is useful in the detection of nano-objects in an industrial, physiological or intracellular medium.

8 Claims, 6 Drawing Sheets

METHOD AND SYSTEM FOR OPTICAL DETECTION OF NANO-OBJECTS IN A LIGHT REFRACTING MEDIUM

BACKGROUND OF THE INVENTION

The invention relates to a method and a system for optical detection of nano-objects in a refracting medium.

In the technical field of nano-sciences, in which the size of objects is an essential feature which characterizes them, techniques or methods for viewing these objects are fundamental.

The optical techniques used for this purpose at the present time are based on the phenomenon of luminescence. Fluorescent molecules have been studied and widely publicized, and are commonly used in the life sciences.

However, the aforesaid fluorescent molecules only allow short periods of observation, because of the phenomenon of photobleaching.

The development of more intense and stable luminescent objects has partially overcome the aforesaid problems, but only at the cost of the introduction of a considerable phenomenon of blinking.

Another method uses the absorption properties of the objects.

At the temperature of liquid helium, isolated molecules were initially detected by an absorption method based on the high quality factor of the zero phonon line, which has a very large absorption cross section of several $10^{-11}$ cm$^2$ at resonance.

Isolated ions or atoms in rf (radio frequency) traps or high quality factor cavities have been detected by the absorption of a probe beam.

As a general rule, particles having a large absorption cross section and short time intervals between successive absorption events can be successfully detected by absorption methods.

More recently, a detection method for this type of particle has been developed for metallic particles. Metallic particles measuring about one nanometer, when excited in the vicinity of their plasmon resonance by an electromagnetic wave, have a relatively large absorption cross section, namely about $8\times10^{-14}$ cm$^2$ for a particle with a diameter of 5 nm, and a fast electron-photon relaxation time of about one picosecond.

Since the luminescence phenomenon of these particles is very weak, almost all of the absorbed electromagnetic energy is converted to heat. The resulting temperature rise causes a change in the local refractive index.

The aforesaid more recent method makes use of a method of interference contrast in polarized light, for detecting this local photothermal effect and displaying images of gold particles 5 nm in diameter have been obtained, with a signal to noise ratio of about 10.

For a more detailed description of the aforesaid method, reference may be made to the article entitled Photo thermal Imaging of Nanometer-Sized Metal Particles Among Scatterers, by David Boyer, Philippe Tamarat, Abdelhamid Maali, Brahim Lounis, and Michel Orrit, in: Science, Volume 297, 16 Aug. 2002, pp. 1160-1163, published by the American Association for the Advancement of Science.

The aforesaid method is satisfactory.

However, since it uses an interferometric method, it requires the provision of precision installations, particularly bulky and heavy optical benches, which are necessary for precision and for the preservation of the phase relations between the laser beams which is essential for distinguishing the interference phenomenon.

This type of installation appears inappropriate for the development of industrial or even laboratory installations which are easy to use.

SUMMARY OF THE INVENTION

The object of the present invention is to overcome the drawbacks of the prior art methods, particularly in terms of the simplification of the necessary installations, with the ultimate aim of substantially facilitating operation on an industrial scale.

Another object of the present invention is to apply a method and a system for optical detection of nano-objects by local photothermal detection, having a sensitivity which is significantly greater than that of the aforesaid method of photothermal detection by interferometry, since the signal to noise ratio can be improved to a ratio of 100, and the size of the particles to be detected can be in the range from 1 to 2 nm.

The method of optical detection of nano-objects in a refractive medium according to the present invention is remarkable in that it consists, at least, in illuminating at least one of the nano-objects and the refractive medium by means of a first coherent electromagnetic wave whose amplitude is periodically modulated, so as to cause electromagnetic energy absorption and produce a modulated change in the refractive index of the refractive medium by increasing the temperature according a specified temperature and refractive index profile, in an area in the vicinity of the nano-object, illuminating this nano-object simultaneously by means of a second coherent electromagnetic wave, forming a probe wave, to generate, by diffusion of this probe wave in this area by the temperature and refractive index profile, an emerging probe wave having at least one intensity component amplitude modulated by a beat at the modulation frequency of the first electromagnetic wave, and detecting in the emerging electromagnetic wave this intensity component amplitude modulated by a beat, thus making it possible to distinguish and represent this nano-object in the refractive medium.

The device for optical detection of nano-objects in a refractive medium according to the present invention is remarkable in that it has at least one means of illuminating at least one of these nano-objects and the refractive medium by means of a first coherent electromagnetic wave whose amplitude is periodically modulated, so as to cause electromagnetic energy absorption and produce a modulated change in the refractive index of this refractive medium by increasing the temperature, according to a specified temperature and refractive index profile, in an area in the vicinity of this nano-object, a means for illuminating this nano-object simultaneously by means of a second coherent electromagnetic wave, forming a probe wave, to generate, by diffusion of this probe wave in this area by the temperature and refractive index profile, an emerging probe wave having at least one intensity component amplitude modulated by a beat at the modulation frequency of the first electromagnetic wave, and a module for detecting, in this emerging wave, this intensity component amplitude modulated by a beat, thus making it possible to distinguish and represent this nano-object in the refractive medium.

The method and device proposed by the invention can be applied to the detection of absorbent or metallic nano-objects in an industrial or physiological refractive medium, with specific application to the location and representation of these nanoparticles in these media, in the fields of physical chemistry, materials science and the detection of marked biomolecules in physiological or intracellular environments.

BRIEF DESCRIPTION OF THE DRAWINGS

They will be more easily understood with the aid of the following description and the drawings, in which.

DESCRIPTION OF PREFERRED
EMBODIMENTS OF THE INVENTION

Figure 1:
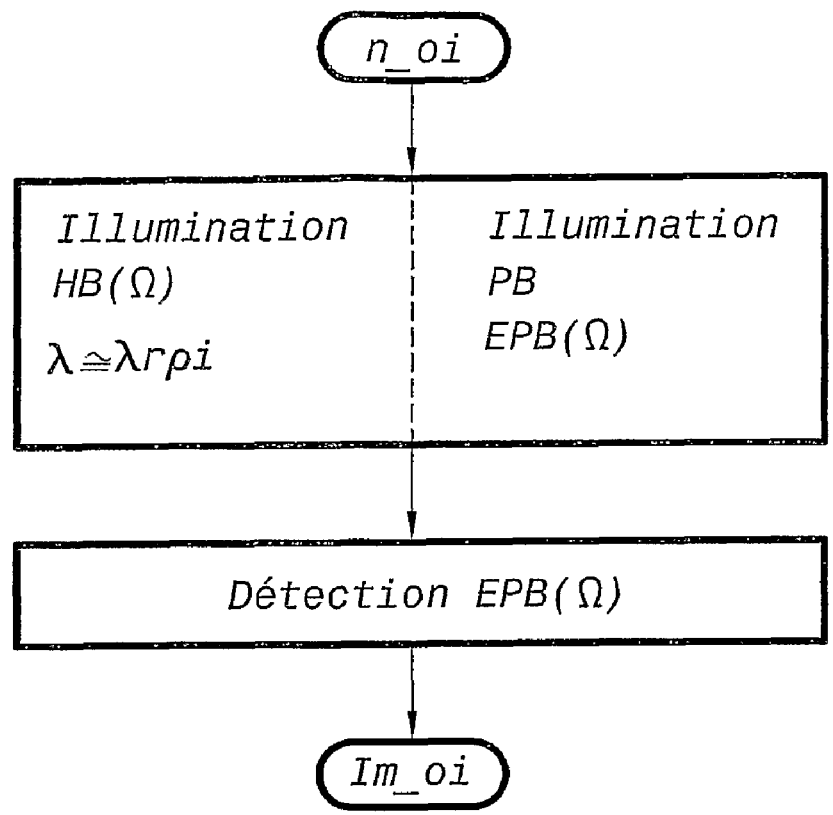
FIG. 1 shows, by way of illustration, a flow chart in the form of a block diagram of the essential steps in the application of the method proposed by the present invention.

A more detailed description of the method for optical detection of nano-objects in a refractive medium proposed by the present invention will now be given in relation to FIG. 1.

With reference to the aforementioned figure, we will consider a plurality of nano-objects, termed $n\_o_i$, in a refractive medium. The aforementioned nano-objects can be in suspension in a liquid refractive medium, for example by placing them on a transparent slide, as described subsequently in the description.

The method proposed by the invention is remarkable in that it comprises a step A of illuminating at least one of the nano-objects $n\_o_i$ and the refractive medium by means of a first periodically amplitude modulated electromagnetic wave, termed HB(O), so as to cause an absorption of electromagnetic energy from the refractive medium and induce a modulated variation of the refractive index of this medium by increasing the temperature.

The amplitude modulation of the first electromagnetic wave is considered to be an intensity modulation at a modulation pulsation termed O. The aforementioned illumination therefore produces a specified temperature and refractive index profile in an area in the vicinity of the nano-object in question, $n\_o_i$.

The method proposed by the invention also comprises the simultaneous illumination, in step B, of the nano-object in question, $n\_o_i$, with a second coherent electromagnetic wave, the aforementioned second coherent electromagnetic wave being intended to form a probe wave.

The aforementioned probe wave can be used to generate, by diffusion of the wave in the area to which the temperature and refractive index profile relates, an emerging probe wave termed EPB(O) having at least one intensity component amplitude modulated by a beat at the modulation frequency of the first electromagnetic wave.

In particular, because of the modulated variation of the refractive index of the refractive medium, the probe wave PB is clearly subjected to a phenomenon of diffusion or dispersion.

The method proposed by the invention then continues with a step C, in which the intensity component, amplitude modulated by a beat, is detected in the emerging wave EPB(O).

Clearly, therefore, the aforementioned detection makes it possible to distinguish and represent the nano-object $n\_O_i$ in the refractive medium in the form of an image $I_{n \rightarrow oi}$ by the variation of luminous intensity of the emerging probe wave EPB(O), which has a peak in the vicinity of the nano-object in question in the area of the vicinity of this object.

The combination of the physical processes used by the method proposed by the present invention is explained below. The nano-object in question, introduced into a homogeneous refractive medium, when the medium is illuminated by the first amplitude modulated coherent electromagnetic wave, behaves as a point source of heat with a heating power of the following form:

$$P_{heat}[1+\cos(\Omega t)] \quad (1)$$

In this relation, O is the modulation pulsation of the first coherent electromagnetic wave, and $P_{heat}$ is the mean heating power of the absorbed coherent electromagnetic wave.

The aforementioned point source of heat generates a time modulation of the refractive index in the vicinity of the nano-object in question, according to a space-time profile given by the relation:

$$\Delta n(r,t) = \frac{\partial n}{\partial T} \frac{P_{heat}}{4\pi k r}\left[1 + \cos\left(Ot - \frac{r}{R_{th}}\right) e^{-\frac{r}{R_{th}}}\right] \quad (2)$$

In the above relation, r is the distance to the centre of the nano-object $n\_o_i$;

n is the refractive index of the refractive medium;

$\partial n/\partial t$ is the partial derivative of the refractive index as a function of the temperature, and is about $10^{-4}$/K;

$R_{th}=\sqrt{2\kappa/OC}$ is the length or characteristic radius of heat diffusion, where $\kappa$ is the thermal conductivity of the refractive medium and C is its specific heat per unit volume.

In these conditions, the probe beam propagated in the area in the vicinity of the illuminated particle, and of course in the corresponding refractive medium with a modulated refractive index according to the corresponding refractive index profile, generates a diffused electromagnetic probe wave having side bands frequency shifted by the frequency of the amplitude modulation of the first coherent electromagnetic wave.

The refractive medium with a variable refractive index in the area in the vicinity of the nano-object in question causes, by a heterodyning phenomenon between the reflected or transmitted incident probe beam PB and the diffused coherent electromagnetic probe wave, a beat frequency at the modulation pulsation O, which can be detected by a conventional detection method.

The intensity component amplitude modulated by a beat can therefore be detected in the emerging probe wave reflected by the refractive medium or in the emerging probe wave transmitted by the refractive medium.

The aforementioned conventional detection methods can advantageously include synchronous detection, which makes it possible to reduce the noise level and consequently to optimize the signal to noise ratio of the resulting signal, following the detection of the intensity component amplitude modulated by a beat.

In general, it should be noted that the method proposed by the present invention is applicable to the optical detection of nano-objects, regardless of whether these nano-objects are absorbent or metallic, such as aggregates of gold atoms, as described subsequently in this description.

If the nano-objects are metallic, for example when metallic particles with diameters of a few nanometres are used for marking cells in an intracellular medium, the wavelength of the first coherent electromagnetic wave is set at a value close to the plasmon resonance wavelength of the nano-object in question.

In all cases, regardless of the type of nano-object to be detected, according to the method proposed by the present invention, the second electromagnetic wave forming a probe beam is focused in the area in the vicinity of the nano-object in a similar way to the focusing of the first electromagnetic wave.

Tests were conducted in the following conditions.

Metallic nanospheres, namely gold nanospheres, were diluted in an aqueous solution of PVOH (2% by weight) and deposited on a microscope slide by what is known as the "spincoating" method. The resulting surface density, of less than 1 $\mu m^{-2}$, was low enough for there to be less than one particle per Airy disc by averaging at the focal point of the coherent electromagnetic waves.

The first coherent electromagnetic wave at 532 nm was amplitude modulated at a frequency of about 1 MHz. The aforementioned wavelength of 532 nm is located in the vicinity of the plasmon resonance of the gold nanospheres. In these conditions, the nanospheres strongly absorb the electromagnetic heating energy and therefore act as a point source at the origin of a local temperature variation modulated at the frequency $\Omega/2\rho$.

In order to provide a refractive medium which could be modelled in terms of its physical properties, a layer of silicone oil (30,000 mPa·s) with a refractive index n=1.4 was also deposited on the specimen.

In these conditions, the temperature profile in the area in the vicinity of each nano-object has spherical symmetry and is characterized by the aforementioned length $R_{th}$. By superimposing the coherent electromagnetic probe wave at 633 nm on the electromagnetic heating wave, and focusing the waves in the vicinity of a gold nanosphere, in other words typically at a distance of less than the length or radius of heat diffusion $R_{th}$, a disturbance can be introduced into the propagation of the probe beam by means of the fluctuations modulated at the pulsation O of the refractive index of the medium, induced by the heating caused by the nano-object.

Thus the emerging probe wave is composed of the interaction of a continuous component with a very low intensity component modulated at the pulsation O arising from the diffusion of the probe beam EPB by the temperature profile in the vicinity of the nano-object.

The aforementioned tests made it possible to map specimens including nano-objects with a size of 1 nm and thus to characterize the dependence of the detected signal in relation to the various test parameters, such as the heating power, the modulation frequency and the size of each nano-object.

A more detailed description of a device for optical detection of nano-objects in a refractive medium according to the object of the present invention will now be given in relation to FIG. 2a.

As shown in the aforementioned figure, the device for optical detection of nano-objects in a refractive medium proposed by the present invention has at least means 1 for illuminating at least one of the nano-objects $n\_o_i$ and the refractive medium by means of a first coherent electromagnetic wave HB periodically amplitude modulated at the pulsation O. This makes it possible to cause an absorption of electromagnetic energy and to induce a modulated variation of the refractive index of the refractive medium by increasing the temperature, according to a specified temperature and refractive index profile, in an area in the vicinity of the nano-object in question, as mentioned previously in the description.

The device proposed by the invention also has means 2 for simultaneously illuminating the nano-object $n\_o_i$ in question with a second coherent electromagnetic wave PB, forming a probe wave, to generate in the area in the vicinity of the nano-object $n\_o_i$, by the diffusion of this wave in this area, by the aforementioned temperature and refractive index profile, an emerging probe wave EPB(O) having at least one intensity component amplitude modulated by a beat at the modulation frequency of the first electromagnetic wave.

Finally, the device proposed by the invention has at least means 3 for detecting the intensity component amplitude modulated by a beat in the emerging wave EPB(O).

This operating mode can be used to distinguish and represent the nano-object in the refractive medium in the form of an image of the refractive medium in question.

Figure 2A:
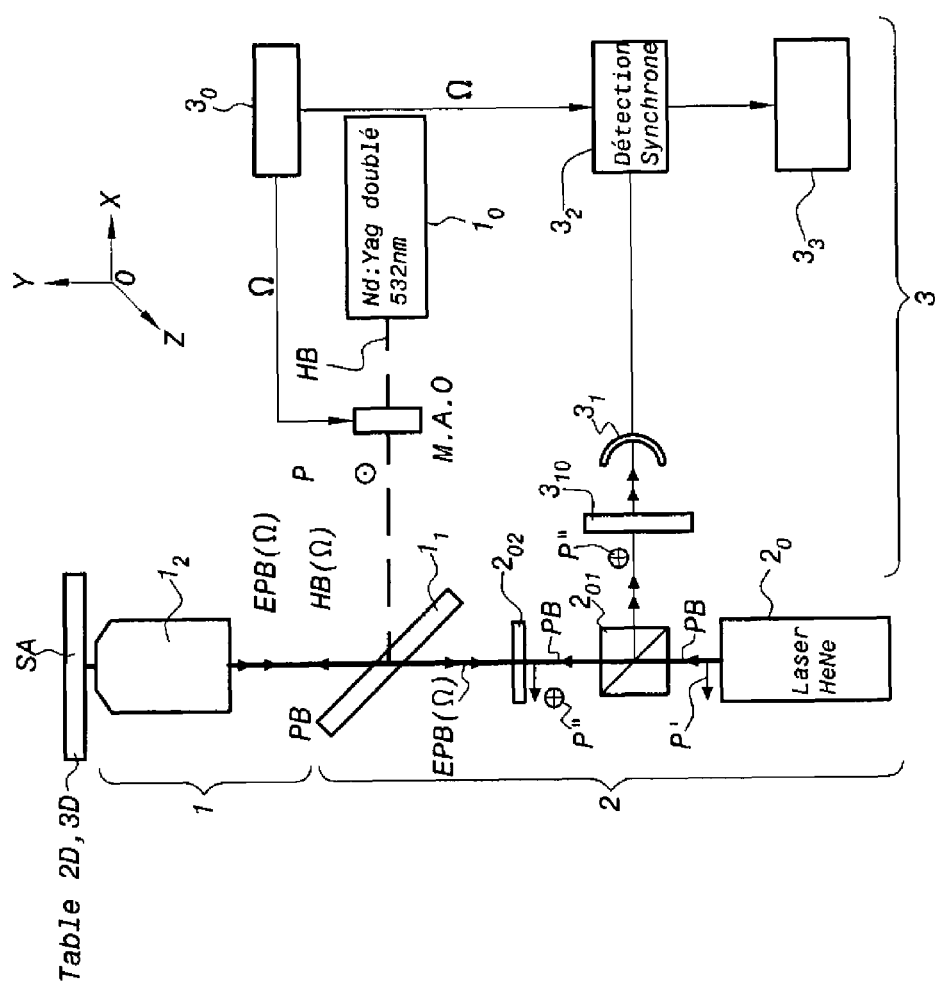
FIG. 2a shows, by way of illustration, an example of the use of a device for optical detection of nano-objects as proposed by the present invention.

As shown in the aforementioned FIG. 2a, the means 1 for illumination with the first coherent electromagnetic wave comprises at least one generator $1_0$ of a first laser beam forming the first coherent electromagnetic wave to form a heating wave. The laser generator $1_0$ can advantageously be an Nd:Yag laser generator frequency-doubled at 532 nm.

The illumination means 1 also includes a device, indicated by $1_2$, for focusing the first laser beam forming the first electromagnetic wave on the nano-object in the refractive medium.

The first heating laser beam at the pulsation O is modulated by means of an acousto-optic modulator $1_{03}$, which is controlled by a control generator, indicated by the reference $3_0$ in FIG. 2a. This generator delivers acousto-optical modulator control signals at the pulsation O. The acousto-optic modulator is a modulator of a conventional type, and therefore it will not be described in detail.

As also shown in FIG. 2a, the means 2 for the simultaneous illumination of the nano-object in question by a second electromagnetic wave PB forming the probe wave has at least one generator $2_0$ of a second laser beam, for example an HeNe laser for forming the probe wave.

The second laser beam generated by the laser generator $2_0$ is then focused on the nano-object in question in the refractive medium in the following conditions, shown in FIG. 2a.

The modulated heating wave HB(O) and the probe wave PB are superimposed by means of a dichroic mirror $1_1$ on a common optical path formed between the aforementioned dichroic mirror and a single common objective, in other words the objective $1_2$ which was mentioned previously in the description and which forms the focusing device.

Finally, the first laser beam HB is linearly polarized because it is emitted in a direction P perpendicular to the surface of FIG. 2a, for example.

The second laser beam forming the probe wave is linearly polarized on emission by the laser source $2_0$ in a second direction P', which for example lies in the plane of the surface of FIG. 2a.

The direction of polarization of the probe wave emitted by the laser source $2_0$ is then converted to a circular polarization PC in a plane orthogonal to the surface of FIG. 2a, by means of a λ/4 blade indicated by $2_{02}$ in the aforementioned figure. The aforementioned circular polarization is transmitted by the dichroic mirror. After focusing on the specimen SA shown in FIG. 2a and the transmission of the emerging probe wave EPB(O), the circular polarization is substantially conserved and the transmission by the λ/4 blade, indicated by $2_{02}$, of the emerging probe wave EPB(O) enables a linear polarization of this wave to be restored in a third direction P''' orthogonal to the second direction P' of polarization of the initial probe wave PB. The second and third directions are thus contained in a plane orthogonal to the surface of FIG. 2a, as shown in the aforementioned figure.

A polarization separator device $2_{01}$ formed by a polarization separator cube can then be used to restore only the emerging probe wave EPB(O) polarized in a direction P''' orthogonal to the plane of the surface of FIG. 2a, forming the third of the aforementioned directions.

The polarization separator device $2_{01}$ is placed on the optical path common to the emerging probe wave linearly polarized in the third direction P''' and the probe wave polarized in the second direction P'.

Finally, the device proposed by the invention as shown in FIG. 2a has detection means 3, which comprise at least one photodiode $3_1$ receiving the emerging probe wave EPB(O). The aforementioned photodiode is advantageously a low-noise photodiode, the emerging probe wave EPB(O) also being received by means of a high-pass filter $3_{10}$.

The detection means also has, as shown in the aforementioned figure, a detection synchronization module which receives a detection signal delivered by the photodiode $3_1$ and a synchronous detection control signal for the periodic amplitude modulation of the first laser beam.

For this purpose, the modulation signal generator $3_0$ delivers a signal representing the periodic modulation O to a detection synchronization device $3_2$, which can be used for synchronous detection of the signals delivered by the photodiode $3_1$ for display by an imaging system $3_3$. The synchronization device $3_2$ can be, for example, a lock-in amplifier.

Finally, it should be noted that the system composed of the focusing device $1_2$, and of course the dichroic mirror $1_1$, the laser generators $1_0$ and $2_0$, and the optical components, namely the acousto-optic modulators $1_{03}$, the dichroic mirror $1_1$, the λ/4 blade $2_{02}$, the polarization separator cube $2_{01}$, the high-pass filter $3_{10}$ and the photodiode $3_1$ are fixed.

To obtain a two-dimensional image, or if necessary a plurality of two-dimensional images forming sections through a three-dimensional object, the specimen SA, which is the preparation described previously, is advantageously placed on a three-dimensional piezoelectric platform, as indicated, for example, by the frame of reference OXYZ.

Details of the operating mode of the device proposed by the present invention, according to the method described above in the description, will now be given.

An estimate of the detected signal measured by synchronous detection was obtained by using the theory of diffusion in a variable dielectric medium, to calculate the electromagnetic field diffused by the refractive index profile obtained in the vicinity of each nano-object and defined by the aforementioned relation 2.

The beat at the pulsation O between the reference probe wave PB and the diffused probe wave gives rise to a beat energy S in the synchronous detector, according to the following relation and having two terms in quadrature:

$$S = \alpha n \frac{\partial n}{\partial T} \sqrt{I_{inc}} \sqrt{P_{ref}} \frac{P_{heat}}{C\lambda^2} \frac{1}{O}[f_k(O)\cos(Ot) + g_k(O)\sin(O)] \quad (3)$$

In the above relation,

α is a shape factor which is close to unity;

$I_{inc}$ is the intensity of the second incident coherent electromagnetic wave, in other words that of the laser beam forming the probe wave;

$P_{ref}$ is the power of the second electromagnetic wave forming the emerging probe wave, reflected in the experimental conditions;

$f_k(O)$ and $g_k(O)$ are two dimensionless functions which depend on the modulation pulsation and on the thermal diffusivity of the refractive medium.

For low modulation pulsations, the characteristic length or radius of thermal diffusion $R_{th}$ is larger than the focusing diameter of the probe beam or wave, and the component $f_k(O)/O$ in phase with the modulation applied to the heating beam is preponderant.

However, for a sufficiently high modulation frequency, such that $R_{th} \ll F$, where F denotes the diameter of the focus spot of the probe wave, the component in quadrature $g_k(O)/O$ becomes preponderant and decreases as 1/O.

The amplitude of the demodulated signal delivered by the synchronous detection device $3_2$ of FIG. 2a obeys the relation:

$$S_{dem} \cong \sqrt{\langle S(t)^2 \rangle}, \cong \frac{1}{O}\sqrt{f_k(O)^2 + g_k(O)^2} \quad (4)$$

In the above relation, the sign ≅ denotes the proportionality of the demodulated signal $S_{dem}$ and $\langle S(t)^2 \rangle$ denotes the square of the amplitude of the beat signal given by the preceding relation 3.

Figure 3A:
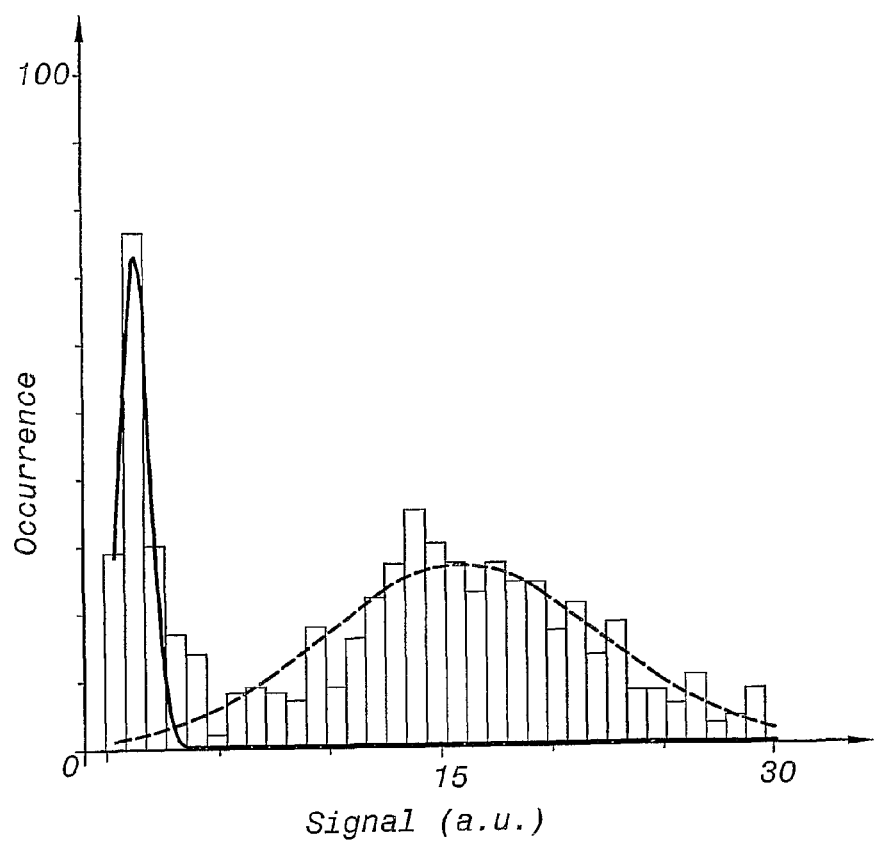
FIG. 3a shows the principle of variation of the detected signal as a function of the modulation frequency.
Figure 3B:
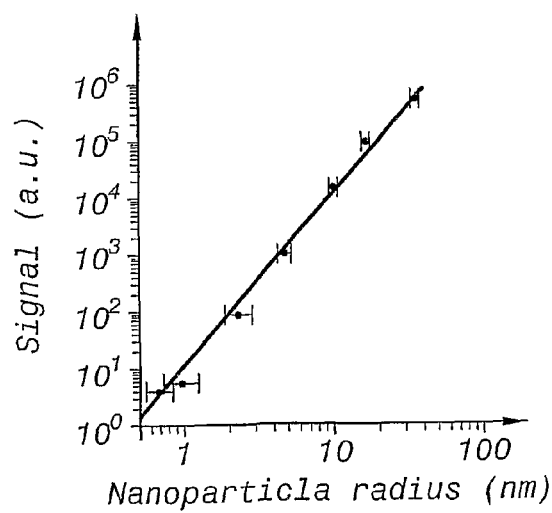
FIG. 3b shows the principle of variation of the absorption cross section as a function of the size (the radius) of the nano-objects.

The variations of $f_k(O)/O$ and $g_k(O)/O$ are shown in FIG. 3a for $K/C = 2 \cdot 10^{-8}$ m²/s.

The aforementioned relation 4 was used to evaluate the energy of the beat component in the detector.

A nano-object consisting of a gold particle with a diameter of 1.4 nm has an absorption cross section of $5 \times 10^{-15}$ cm² at 532 nm, and absorbs a heating power $P_{heat} = 10$ mW, when it is illuminated by a laser beam with an intensity of 2 MW/cm².

For an incident probe beam with a power of $P_{inc} = 70$ mW, for a modulation frequency $\Omega/2\pi = 800$ kHz, and for a reference power $P_{ref} = 100$ μW, the above relation (4) indicates a beat power $S_{dem}$ of 5 mW. After the calibration of the detection circuit, the effective measured value was substantially equal to 2 mW, in other words in accordance with the predicted theoretical value.

Figure 4A:
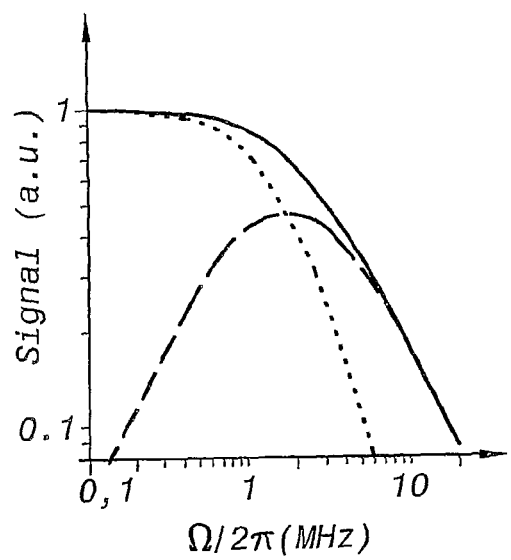
FIG. 4a shows the principle of dependence of the detected signal as a function of the modulation frequency applied to the amplitude of the electromagnetic heating wave.

FIG. 4a shows the variation of the detected signal as a function of the frequency $\Omega/2\pi$ of the modulation of the heating wave. The dotted-line curve shows the variation of the component of the detected signal in phase with the modulation of the heating wave. The mixed-line curve shows the variation of the component of the detected signal in quadrature with the modulation of the heating wave. The solid-line curve shows the total amplitude of the detected signal.

Figure 4B:
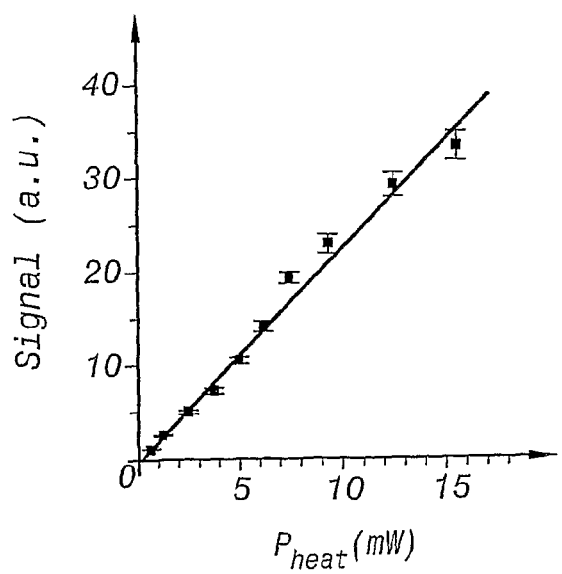
FIG. 4b shows the principle of dependence of the detected signal as a function of the power of the electromagnetic heating wave.

FIG. 4b shows the linear dependence of the signal as a function of the heating power $P_{heat}$ expressed in milliwatts. The amplitude of the signal is given in relative amplitude, in a.u. (absolute units). A further increase in the heating power is not followed by saturation but leads to fluctuations of the amplitude of the detected signal, and, in certain conditions, to irreversible damage to the particle.

Figure 2B:
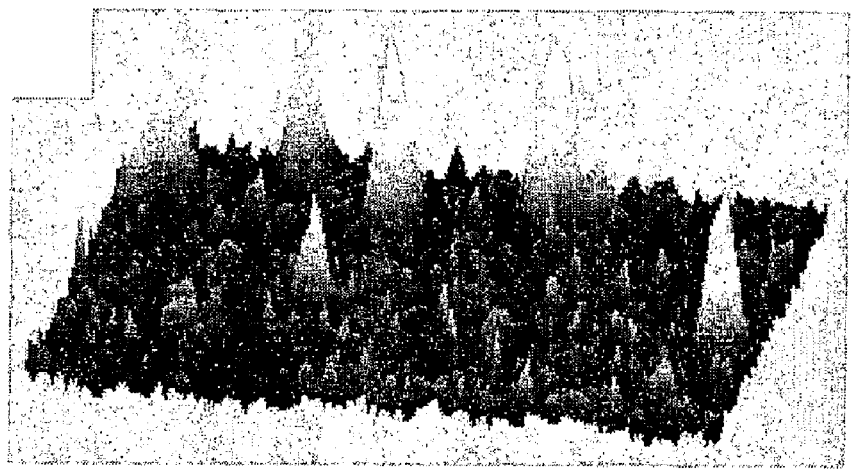
FIG. 2b shows, by way of illustration, a representation of an image of aggregates of 67 gold atoms (1.4 nm) obtained by optical detection, by the application of the method proposed by the present invention.

With reference to FIG. 2b, it should be noted that the method and device proposed by the present invention can be used to detect nano-objects formed by metallic particles with sizes as small as 1.4 nm in diameter with a signal to noise ratio SNR>10.

In practice, a Ti:Sa laser probe wave at 720 nm and a frequency-doubled Nd:Yag laser heating beam at 532 nm, whose intensity was modulated at a pulsation corresponding to a frequency in the range from 100 kHz to 15 MHz by the acousto-optical modulator, were used.

The objective used was a Zeiss 100× objective, nA=1.4. The power of the heating beam was in the range from 1 mW to 3.5 mW, depending on the size of the nano-object to be detected.

An image of the specimen SA was formed by moving the aforementioned specimen with respect to the first and second focused beams which were kept fixed, using the platform 2D.

The specimens SA were prepared, as mentioned above, from a solution of gold particles with diameters of 1.4 nm, 2 nm, 5 nm, 10 nm, 20 nm, 33 nm, 20 nm, 33 nm or 75 nm.

FIG. 2b is a three-dimensional representation of a heterodyned photothermal image, obtained by the application of the method and device proposed by the invention, for aggregates of 1.4 nm gold atoms.

The image revealed the absence of background noise introduced by the substrate, indicating that the detected signal originated solely from the absorbent objects in the specimen, in other words the aggregates of gold particles. These particles were detected with a relatively low heating power of about 3.5 nW, and a remarkable signal to noise ratio of more than 10.

Figure 2C:
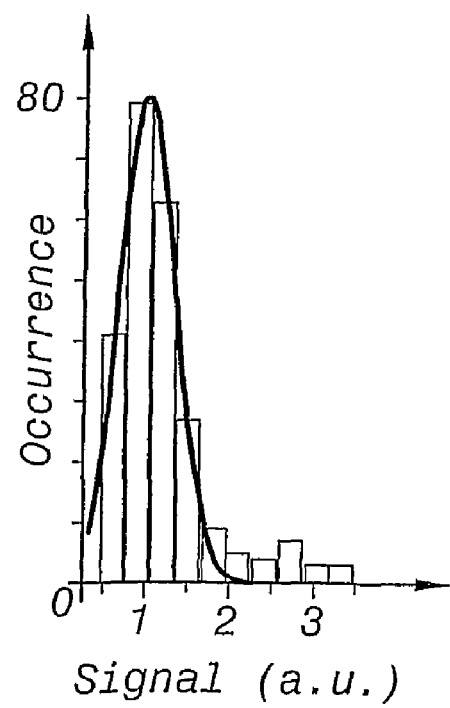
FIG. 2c shows a histogram of the amplitude of the detected signal for a given number of peaks of intensity of the image shown in FIG. 2b.

The histogram of the amplitude of the signal for 272 peaks of intensity of the image of FIG. 2b, shown in FIG. 2c, demonstrates that the peaks of amplitude of luminous intensity arise from the nano-objects themselves.

The capture cross section of the aforementioned aggregates reaches a maximum of about $10^{-15}$ cm$^2$, comparable with that of good fluorophores or CbSe/ZnS nano-crystals. Their relaxation time is very short.

On the other hand, luminescent semiconducting nano-crystals and fluorescent molecules have emission relaxation times of about a nanosecond, making them difficult to detect by absorption.

However, at relatively high excitation intensities, semiconducting nano-crystals cease to show luminescence. The method and device proposed by the present invention can be used to detect nano-objects having a short emission relaxation time.

Figures 5A, 5B:
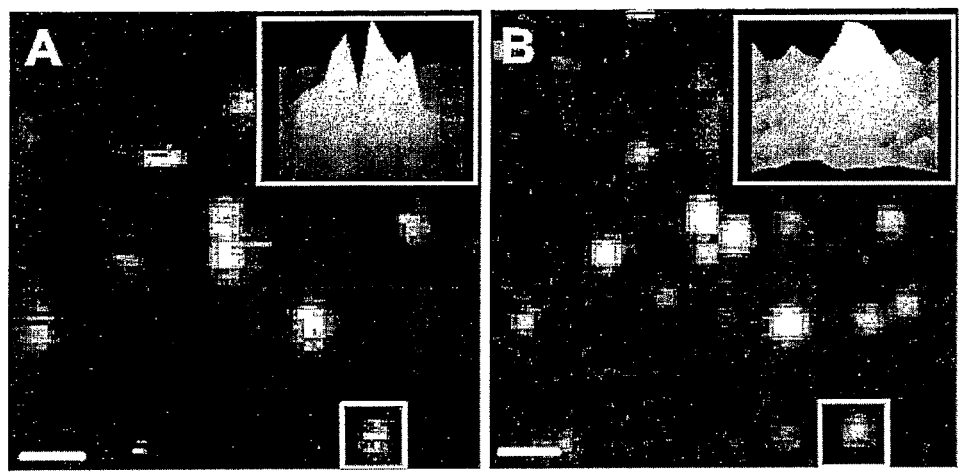
FIG. 5a shows the fluorescence image of a preparation of colloidal CdSe/ZnS containing quantum boxes and excited by an electromagnetic heating wave at a very low power density.
FIG. 5b shows, for comparison, the image of the same preparation, obtained by the application of the method proposed by the present invention, in which the quantum boxes are detected and distinguished.

FIG. 5a shows the fluorescent image of quantum boxes of luminescent colloidal CdSe/Zns, whose emission peak is at 640 nm, excited by the heating beam at a very low intensity of about 0.1 kW/cm$^2$. The blinking behaviour, characteristic of single quantum box emission, is visible in this image.

On the other hand, FIG. 5b shows an image of the same region obtained by the application of the method and device proposed by the present invention, at an excitation intensity of 5 MW/cm$^2$, for which the quantum boxes are no longer luminescent.

The two images are correctly correlated, thus ensuring that the amplitudes of intensity in the image of FIG. 5b, obtained by the application of the method proposed by the present invention, are actually due to individual quantum boxes. These no longer show any blinking. In a particularly remarkable way, quantum boxes which were initially non-fluorescent, in other words absent from FIG. 5a, are now detected and shown in FIG. 5b.

Finally, it should be noted that, for the use of the method and device proposed by the present invention in biological or life science applications, the temperature increase at the surface of the nano-objects is an important parameter.

In a widely used configuration, a nano-object in the form of a gold particle with a diameter of 5 nm can be detected with a signal to noise ratio of >100, for a heating power of 1 mW.

In these conditions, the local temperature increase can be estimated at 4 K in an aqueous solution.

Since the temperature decreases as the inverse of distance, and most applications for detecting elements or organelles in the life sciences do not require anything like such a high signal to noise ratio, it should be noted here that the method and device proposed by the present invention can be used to detect and represent in an electronic image very small gold particles or nano-object, while the induced local heating can be made substantially lower than 1 K, above the mean temperature of the specimen.

Finally, as regards the simplification of the device proposed by the invention as shown in FIG. 2a, by comparison with the device shown in the article mentioned in the description, it may be noted that the superfluous telecentric device has been eliminated. This is due to the fact that, in the method and the device proposed by the present invention, the interaction between the reference diffused probe wave and the modulated diffused probe wave generating the component amplitude modulated by a beat at the pulsation O takes place in the area in the vicinity of the nano-object in question.

Conversely, in the device described in this article, the interaction takes place by interference, instead of by a beat, in the Wollaston prism and the detector, making it essential to maintain the phase relations between the split beams and therefore to use the telecentric system, whereas this is not the case with the method and device proposed by the invention.

The invention claimed is:

1. Method of optical detection of nano-objects in a refractive medium, comprising the following steps:
   (a) illuminating at least one of (i) the nano-objects and (ii) the refractive medium with a first coherent electromagnetic wave which is periodically amplitude modulated, so as to cause an absorption of electromagnetic energy and induce a modulated variation of the refractive index of the refractive medium by increasing the temperature, according to a specified temperature and refractive index profile, in an area in the vicinity of the nano-object;
   (b) simultaneously with step (a), forming a probe wave by illuminating the nano-object with a second coherent electromagnetic wave;
   (c) generating an emerging probe wave by diffusion of the formed probe wave in the area by the temperature and refractive index profile, the emerging probe wave having at least one intensity component amplitude modulated by a beat at the modulation frequency of the first electromagnetic wave; and
   (d) detecting in the emerging probe wave the intensity component amplitude modulated by a beat, making it possible to distinguish and represent the non-object in the refractive medium,
   wherein step (a) comprises:

generating a first laser beam forming the first coherent electromagnetic wave forming a heating wave; and focusing the first modulated laser beam on the nano-objects in the refractive medium, wherein step (b) comprises:

generating a second laser beam, forming the probe wave;

focusing the second modulated laser beam on at least one of the nano-objects in the refractive medium; and superimposing the heating wave and the probe wave on a common optical path formed between a dichroic mirror and a single common objective for the step of focusing the second modulated laser beam, wherein step (a) further comprises linearly polarizing the first laser beam in a first direction, and step (b) further comprises linearly polarizing the second laser beam in a second direction, the probe wave being linearly polarized in the second direction; and wherein after step (c), further comprising step (e) of linearly polarizing the emerging probe wave in a third direction orthogonal to the second direction, and between steps (e) and (d), further comprising step (f) of separating by polarization separation the emerging probe wave linearly polarized in the third direction and the probe wave polarized in the second direction, so as to deliver only the emerging probe wave linearly polarized in the third direction.

2. Method according to claim 1, wherein the operation of detecting the intensity component amplitude modulated by a beat is carried out by synchronous detection.

3. Method according to claim 1, wherein, for a metallic nano-object, the wavelength of the first coherent electromagnetic wave is close to the plasmon resonance wavelength of this nano-object.

4. Method according to claim 1, wherein the second electromagnetic wave is focused in the area in the vicinity of the nano-object.

5. Method according to claim 1, wherein the representing step comprises forming a viewable image of the nano-object and refractive medium from the emerging probe wave.

6. Device for optical detection of nano-objects in a refractive medium, comprising:

means for generating a periodically amplitude modulated first coherent electromagnetic wave and for illuminating at least one of (i) the nano-objects and (ii) the refractive medium with the first wave to cause an absorption of electromagnetic energy and induce a modulated variation of the refractive index of the refractive medium by increasing the temperature, according to a specified temperature and refractive index profile, in an area in the vicinity of the nano-object;

means for generating a second coherent electromagnetic wave and for illuminating the nano-object with the second coherent electromagnetic wave simultaneously with illuminating at least one of (i) the nano-objects and (ii) the refractive medium with the first wave, thereby forming a probe wave, to generate, by diffusion of this probe wave in the area by the temperature and refractive index profile, an emerging probe wave having at least one intensity component amplitude modulated by a beat at the modulation frequency of the first electromagnetic wave; and means for detecting, in the emerging wave, the intensity component amplitude modulated by a beat, making it possible to distinguish and represent the nano-object in the refractive medium, wherein the means for illumination by a first coherent electromagnetic wave comprises:

means for generating a first laser beam forming the first coherent electromagnetic wave forming a heating wave; and means for focusing the first modulated laser beam on the nano-objects in the refractive medium, wherein the means for simultaneous illumination of the nano-object by a second electromagnetic wave comprises:

means for generating a second laser beam, forming the probe wave; and means for focusing the second modulated laser beam on at least one of the nano-objects in the refractive medium, wherein the heating wave and the probe wave are superimposed by means of a dichroic mirror, on a common optical path formed between this dichroic mirror and a single common objective forming the focusing means, wherein, for the detection in the emerging probe wave of the intensity component amplitude modulated by a beat, by reflection, the device additionally comprises:

means for linearly polarizing the first laser beam in a first direction;

means for linearly polarizing the second laser beam in a second direction, the probe wave being linearly polarized in the second direction;

means for linearly polarizing the emerging probe wave in a third direction orthogonal to the second direction; and means for polarization separation placed on the optical path common to the emerging probe wave linearly polarized in the third direction and to the probe wave polarized in the second direction, the separator means making it possible to deliver only the emerging probe wave linearly polarized in the third direction.

7. Device according to claim 6, wherein the detection means include at least one photodiode receiving the emerging probe wave.

8. Device according to claim 7, wherein the detection means additionally include a detection synchronization module receiving a detection signal delivered by the photodiode, and a control signal for the synchronous detection of the periodic amplitude modulation of the first laser beam.

* * * * *